(12) United States Patent
Clarke et al.

(10) Patent No.: US 12,201,751 B2
(45) Date of Patent: Jan. 21, 2025

(54) FLUSHABLE DISINTEGRATION CATHETER

(71) Applicant: Hollister Incorporated, Libertyville, IL (US)

(72) Inventors: John T. Clarke, Galway (IE); Jerome A. Henry, Castlebar (IE); Adam J. Foley, Swords (IE); Shamsedin Rostami, South (GB); Enda F. Carter, Galway (IE); Horacio Montes de Oca Balderas, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 195 days.

(21) Appl. No.: 17/101,388

(22) Filed: Nov. 23, 2020

(65) Prior Publication Data

US 2021/0069385 A1 Mar. 11, 2021

Related U.S. Application Data

(62) Division of application No. 15/103,399, filed as application No. PCT/US2014/069530 on Dec. 10, 2014, now Pat. No. 10,874,769.

(Continued)

(51) Int. Cl.
*A61L 29/14* (2006.01)
*A61L 29/02* (2006.01)
(Continued)

(52) U.S. Cl.
CPC .............. *A61L 29/14* (2013.01); *A61L 29/02* (2013.01); *A61L 29/041* (2013.01);
(Continued)

(58) Field of Classification Search
CPC ........ A61L 29/02; A61L 29/041; A61L 29/14; A61L 29/148; A61M 25/0009; A61M 25/0017; A61M 25/002; A61M 25/0043
See application file for complete search history.

(56) References Cited

U.S. PATENT DOCUMENTS 3,583,391 A 6/1971 Cox
3,621,848 A 11/1971 Magovern
(Continued)

FOREIGN PATENT DOCUMENTS

CN 2240371 Y 11/1996
CN 101300036 A 11/2008
(Continued)

OTHER PUBLICATIONS

A.K. Singla, M. Chawla, Chitosan some pharmaceutical and biological aspects, an update, Journal of Pharmacy and Pharmacology, Aug. 2001, 53: 1047-1067.
(Continued)

*Primary Examiner* — Kai H Weng
(74) *Attorney, Agent, or Firm* — Cook Alex Ltd.

(57) ABSTRACT

Medical devices that are flushable in a standard toilet are disclosed. The medical devices are made at least in part of material that when introduced into water (of a toilet) disintegrate and/or fragment or are fragmentable before or after introduction into water such that they can be easily carried by the water through the disposal system. At least a portion of the device is intended for insertion into a patient or subject wherein the body-insertable portion retains its structural integrity while in use but is fragmentable once outside the body and exposed to a selected condition.

24 Claims, 3 Drawing Sheets

Related U.S. Application Data

(60) Provisional application No. 62/011,337, filed on Jun. 12, 2014, provisional application No. 61/915,311, filed on Dec. 12, 2013, provisional application No. 61/915,396, filed on Dec. 12, 2013.

(51) Int. Cl.
| | |
|---|---|
| *A61L 29/04* | (2006.01) |
| *A61M 25/00* | (2006.01) |
| *B29B 15/00* | (2006.01) |
| *B29C 44/02* | (2006.01) |
| *B29L 31/00* | (2006.01) |

(52) U.S. Cl.
CPC ....... *A61L 29/148* (2013.01); *A61M 25/0009* (2013.01); *A61M 25/0017* (2013.01); *A61M 25/002* (2013.01); *A61M 25/0043* (2013.01); *B29B 15/00* (2013.01); *B29C 44/02* (2013.01); *B29K 2995/006* (2013.01); *B29L 2031/7542* (2013.01)

(56) References Cited

U.S. PATENT DOCUMENTS

| | | |
|---|---|---|
| 3,702,610 A | 11/1972 | Sheppard et al. |
| 3,861,396 A | 1/1975 | Vaillancourt et al. |
| 3,894,540 A | 7/1975 | Bonner, Jr. |
| 4,062,363 A | 12/1977 | Bonner, Jr. |
| 4,100,309 A | 7/1978 | Micklus et al. |
| 4,227,533 A | 10/1980 | Godfrey |
| 4,413,986 A | 11/1983 | Jacobs |
| 4,465,481 A | 8/1984 | Blake |
| 4,571,241 A | 2/1986 | Christopher |
| 4,610,671 A | 9/1986 | Luther |
| 4,668,221 A | 5/1987 | Luther |
| 4,762,738 A | 8/1988 | Keyes et al. |
| 4,769,005 A | 9/1988 | Ginsburg et al. |
| 4,772,279 A | 9/1988 | Brooks et al. |
| 4,790,817 A | 12/1988 | Luther |
| 4,790,831 A | 12/1988 | Skribiski |
| 4,795,439 A | 1/1989 | Guest |
| 4,840,622 A | 6/1989 | Hardy |
| 4,883,699 A | 11/1989 | Aniuk et al. |
| 4,906,238 A | 3/1990 | Greenfeld et al. |
| 4,952,359 A | 8/1990 | Wells |
| 4,954,129 A | 9/1990 | Giuliani et al. |
| 4,994,047 A | 2/1991 | Walker et al. |
| 5,002,526 A | 3/1991 | Herring |
| 5,009,648 A | 4/1991 | Aronoff et al. |
| 5,089,535 A | 2/1992 | Malwitz et al. |
| 5,098,535 A | 3/1992 | Nakakoshi et al. |
| 5,102,401 A | 4/1992 | Lambert et al. |
| 5,195,962 A | 3/1993 | Martin et al. |
| 5,270,086 A | 12/1993 | Hamlin |
| 5,439,454 A | 8/1995 | Lo et al. |
| 5,468,526 A | 11/1995 | Allen et al. |
| 5,472,417 A | 12/1995 | Martin et al. |
| 5,569,219 A | 10/1996 | Hakki et al. |
| 5,601,538 A | 2/1997 | Deem |
| 5,616,126 A | 4/1997 | Malekmehr et al. |
| 5,688,459 A | 11/1997 | Mao et al. |
| 5,776,611 A | 7/1998 | Elton et al. |
| 5,792,114 A | 8/1998 | Fiore |
| 5,800,412 A | 9/1998 | Zhang et al. |
| 5,804,653 A | 9/1998 | Weng |
| 5,904,703 A | 5/1999 | Gilson |
| 5,985,394 A | 11/1999 | Mao et al. |
| 6,017,334 A | 1/2000 | Rawls |
| 6,030,369 A | 2/2000 | Engelson et al. |
| 6,063,063 A | 5/2000 | Harboe et al. |
| 6,066,120 A | 5/2000 | Whiteside |
| 6,071,618 A | 6/2000 | Cook, Jr. et al. |
| 6,090,075 A | 7/2000 | House |
| 6,213,990 B1 | 4/2001 | Roempke |
| 6,217,569 B1 | 4/2001 | Fiore |
| 6,447,835 B1 | 9/2002 | Wang et al. |
| 6,468,245 B2 | 10/2002 | Alexandersen |
| 6,471,684 B2 | 10/2002 | Dulak et al. |
| 6,488,659 B1 | 12/2002 | Rosenman |
| 6,585,721 B2 | 7/2003 | Fiore |
| 6,627,586 B1 | 9/2003 | Brooks et al. |
| 6,656,146 B1 | 12/2003 | Clayman et al. |
| 6,664,333 B2 | 12/2003 | Wang et al. |
| 6,713,140 B2 | 3/2004 | McCormack et al. |
| 6,726,654 B2 | 4/2004 | Rosenman |
| 6,942,635 B2 | 9/2005 | Rosenblatt et al. |
| 6,960,224 B2 | 11/2005 | Marino et al. |
| 6,976,973 B1 | 12/2005 | Ruddell et al. |
| 7,037,295 B2 | 5/2006 | Tiernan et al. |
| 7,128,862 B2 | 10/2006 | Wang |
| 7,156,824 B2 | 1/2007 | Rosenman |
| 7,182,906 B2 | 2/2007 | Chen |
| 7,402,620 B2 | 7/2008 | McGhee |
| 7,553,923 B2 | 6/2009 | Williams et al. |
| 7,601,158 B2 | 10/2009 | House |
| 7,641,757 B2 | 1/2010 | Kampa et al. |
| 7,662,146 B2 | 2/2010 | House |
| 7,731,740 B2 | 6/2010 | LaFont et al. |
| 7,789,873 B2 | 9/2010 | Kubalak et al. |
| 7,815,628 B2 | 10/2010 | Devens, Jr. |
| 7,820,284 B2 | 10/2010 | Terry |
| 7,824,517 B2 | 11/2010 | Kampa et al. |
| 7,833,280 B2 | 11/2010 | Stack et al. |
| 7,947,031 B2 | 5/2011 | DiMatteo et al. |
| 8,143,368 B2 | 3/2012 | Domb et al. |
| 8,168,249 B2 | 5/2012 | Utas et al. |
| 8,187,254 B2 | 5/2012 | Hissink et al. |
| 8,388,583 B2 | 3/2013 | Stout et al. |
| 8,388,585 B2 | 3/2013 | Tomes et al. |
| 8,418,019 B2 | 4/2013 | Ivkovic et al. |
| 8,469,928 B2 | 6/2013 | Stout et al. |
| 8,569,402 B2 | 10/2013 | Henderson et al. |
| 2002/0016574 A1 | 2/2002 | Wang et al. |
| 2003/0165647 A1 | 9/2003 | Kaneko et al. |
| 2003/0187368 A1 | 10/2003 | Sata et al. |
| 2003/0228434 A1 | 12/2003 | Bailey et al. |
| 2004/0005362 A1* | 1/2004 | Taneja ............. A61P 1/04 |
| | | 424/489 |
| 2004/0122382 A1 | 6/2004 | Johnson et al. |
| 2004/0210180 A1 | 10/2004 | Altman |
| 2004/0220550 A1 | 11/2004 | Schryver |
| 2004/0230177 A1 | 11/2004 | DiMatteo et al. |
| 2004/0232589 A1 | 11/2004 | Kawabata et al. |
| 2005/0049577 A1 | 3/2005 | Snell et al. |
| 2005/0109648 A1 | 5/2005 | Kerzman et al. |
| 2005/0131386 A1 | 6/2005 | Freeman et al. |
| 2005/0163844 A1 | 7/2005 | Ashton |
| 2005/0197627 A1 | 9/2005 | Huang et al. |
| 2005/0218154 A1 | 10/2005 | Selsby |
| 2005/0277862 A1 | 12/2005 | Anand |
| 2005/0283111 A1 | 12/2005 | Maurice |
| 2006/0173422 A1 | 8/2006 | Reydel et al. |
| 2006/0240064 A9 | 10/2006 | Hunter et al. |
| 2006/0263404 A1* | 11/2006 | Nielsen ............ A61M 25/0045 |
| | | 424/422 |
| 2006/0276894 A1* | 12/2006 | Finley ............. A61L 29/14 |
| | | 623/11.11 |
| 2007/0043333 A1 | 2/2007 | Kampa et al. |
| 2007/0078412 A1 | 4/2007 | McGuckin, Jr. et al. |
| 2007/0088330 A1 | 4/2007 | House |
| 2007/0203502 A1 | 8/2007 | Makker et al. |
| 2007/0225649 A1 | 9/2007 | House |
| 2008/0015527 A1 | 1/2008 | House |
| 2008/0091145 A1 | 4/2008 | House |
| 2008/0097411 A1 | 4/2008 | House |
| 2008/0118544 A1 | 5/2008 | Wang |
| 2008/0147049 A1 | 6/2008 | House et al. |
| 2008/0171991 A1 | 7/2008 | Kourakis |
| 2008/0171998 A1 | 7/2008 | House |
| 2008/0172042 A1 | 7/2008 | House |
| 2008/0183262 A1 | 7/2008 | Dowling |
| 2008/0187628 A1* | 8/2008 | Champion ............ A23L 27/72 |
| | | 426/71 |

(56) References Cited

U.S. PATENT DOCUMENTS

| | | |
|---|---|---|
| 2008/0255510 A1 | 10/2008 | Wang |
| 2008/0268193 A1 | 10/2008 | Cherry et al. |
| 2008/0292776 A1 | 11/2008 | Dias et al. |
| 2008/0312550 A1 | 12/2008 | Nishtala et al. |
| 2009/0018530 A1 | 1/2009 | Nielsen et al. |
| 2009/0036874 A1 | 2/2009 | Horowitz et al. |
| 2009/0204052 A1 | 8/2009 | Nimkar et al. |
| 2009/0250370 A1 | 10/2009 | Whitchurch |
| 2009/0264869 A1 | 10/2009 | Schmid et al. |
| 2010/0030197 A1 | 2/2010 | House |
| 2010/0049146 A1 | 2/2010 | Nielsen et al. |
| 2010/0098746 A1 | 4/2010 | King |
| 2010/0100116 A1 | 4/2010 | Brister et al. |
| 2010/0137743 A1 | 6/2010 | Nishtala et al. |
| 2010/0145315 A1 | 6/2010 | House |
| 2010/0198195 A1 | 8/2010 | Nishtala et al. |
| 2010/0204682 A1 | 8/2010 | Tanghoj et al. |
| 2010/0209472 A1 | 8/2010 | Wang |
| 2010/0215708 A1 | 8/2010 | Zumbuehl et al. |
| 2010/0312255 A1 | 12/2010 | Satake et al. |
| 2010/0323189 A1 | 12/2010 | Illsley et al. |
| 2011/0049146 A1 | 3/2011 | Illsley et al. |
| 2011/0071507 A1 | 3/2011 | Svensson et al. |
| 2011/0114520 A1 | 5/2011 | Matthison-Hansen |
| 2011/0125135 A1 | 5/2011 | Ahmed et al. |
| 2011/0160662 A1 | 6/2011 | Stout et al. |
| 2011/0178425 A1 | 7/2011 | Nishtala et al. |
| 2011/0212157 A1 | 9/2011 | Edelson et al. |
| 2011/0238163 A1 | 9/2011 | Andrews et al. |
| 2011/0268938 A1 | 11/2011 | Schuhmann |
| 2012/0035530 A1 | 2/2012 | Wang |
| 2012/0121919 A1 | 5/2012 | Nielsen |
| 2013/0131646 A1 | 5/2013 | Gilman |
| 2013/0345681 A1 | 12/2013 | Hong et al. |

FOREIGN PATENT DOCUMENTS

| | | |
|---|---|---|
| DE | 102011119160 A1 | 5/2013 |
| EP | 0010171 A1 | 4/1980 |
| EP | 0166998 A2 | 1/1986 |
| EP | 0613672 A1 | 9/1994 |
| EP | 0628586 A1 | 12/1994 |
| EP | 0692276 A2 | 1/1996 |
| EP | 1062920 A1 | 12/2000 |
| EP | 1110561 A2 | 6/2001 |
| EP | 1415671 A1 | 5/2004 |
| EP | 2026846 | 2/2009 |
| EP | 2301595 A1 | 3/2011 |
| EP | 2520412 A1 | 11/2012 |
| EP | 2609956 A1 | 7/2013 |
| GB | 2083762 A | 3/1982 |
| GB | 2496901 A | 5/2013 |
| JP | S61209655 A | 9/1986 |
| JP | 01136662 | 5/1989 |
| JP | 11151293 | 6/1999 |
| KR | 20000065291 | 11/2000 |
| KR | 100754057 B1 | 8/2007 |
| WO | 8905671 A1 | 6/1989 |
| WO | 9641653 A1 | 12/1996 |
| WO | 1998058989 | 12/1998 |
| WO | 0030696 A1 | 6/2000 |
| WO | 2006055847 A2 | 5/2006 |
| WO | 2006071813 A2 | 7/2006 |
| WO | 2007122269 A1 | 11/2007 |
| WO | 2007140320 A2 | 12/2007 |
| WO | 2010043565 A1 | 4/2010 |
| WO | 2011076211 A1 | 6/2011 |
| WO | 2012163413 A1 | 12/2012 |
| WO | 2012166967 A1 | 12/2012 |
| WO | 2014193402 A1 | 12/2014 |

OTHER PUBLICATIONS

Beom Soo Kim, Jeffrey S. Hrkach, Robert Langer, Biodegradable photo-crosslinked poly(ether-ester) networks for tubricious coatings, Biomaterials, vol. 21, Issue 3, Feb. 2000, pp. 259-265.

FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.

International Preliminary Report on Patentability and Written Opinion of the International Searching Authority for International Application No. PCT/US2014/069530 dated Jun. 14, 2016.

International Search Report and Written Opinion dated May 12, 2015, for International Application No. PCT/US2014/069530.

Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.

* cited by examiner

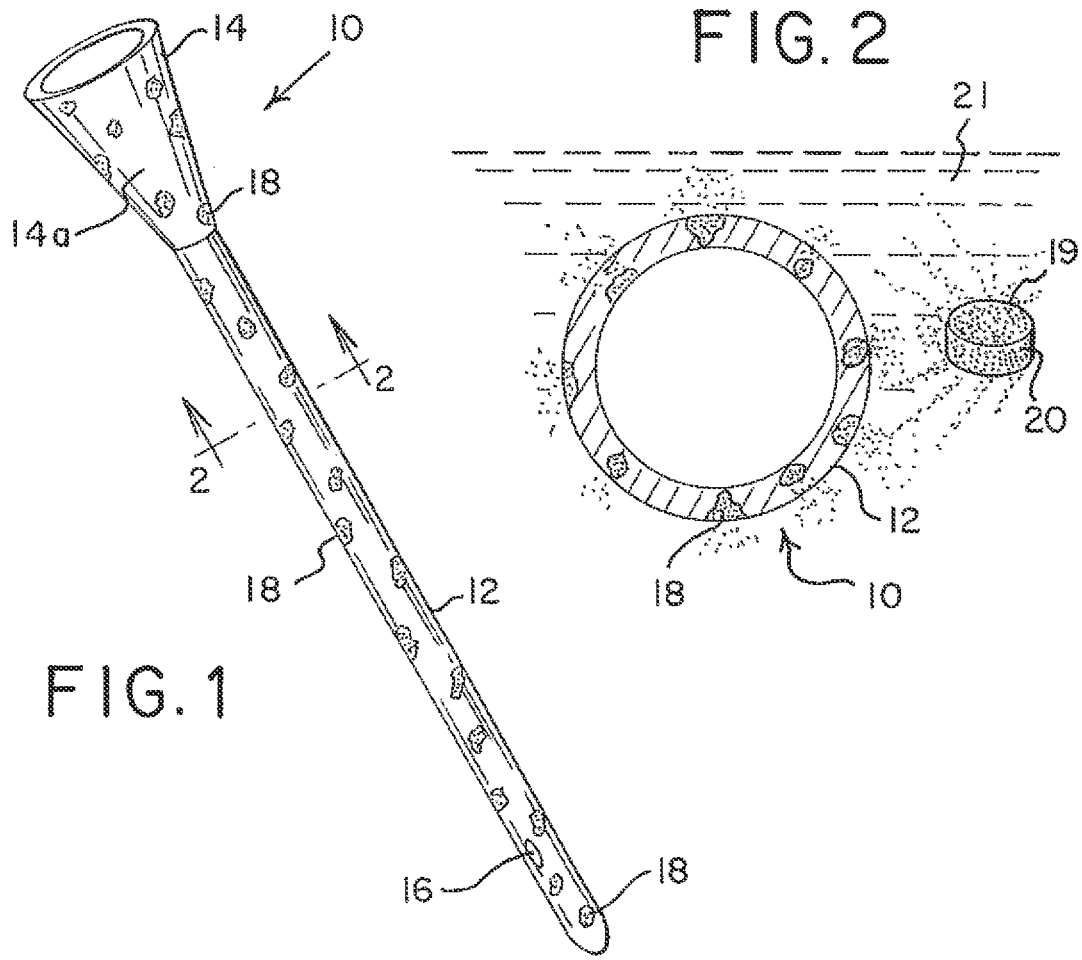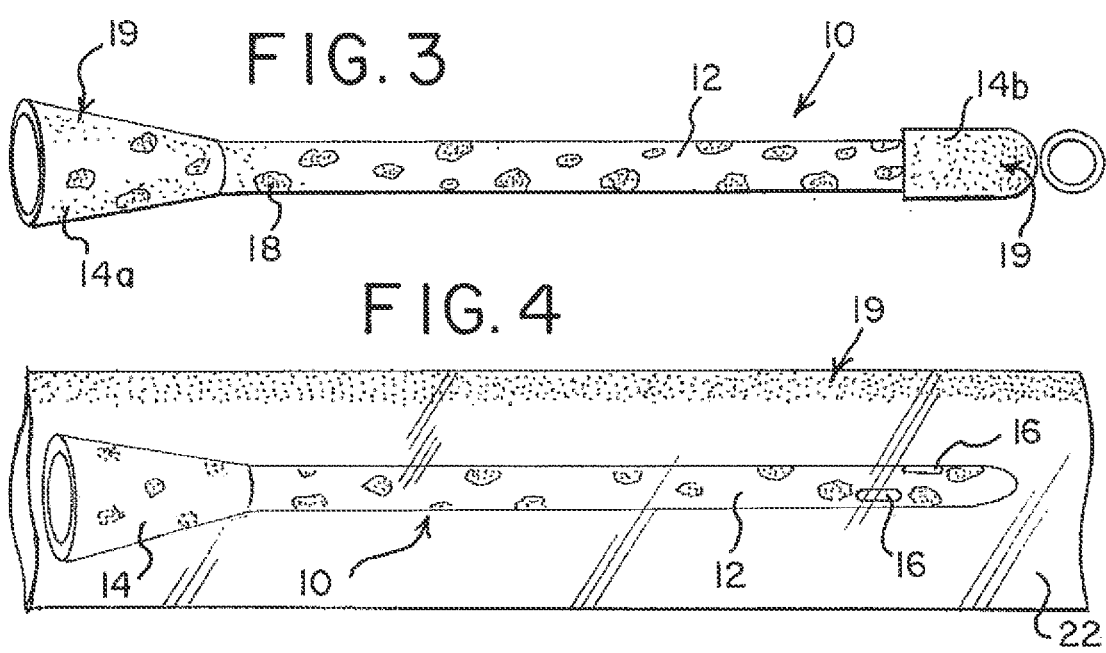

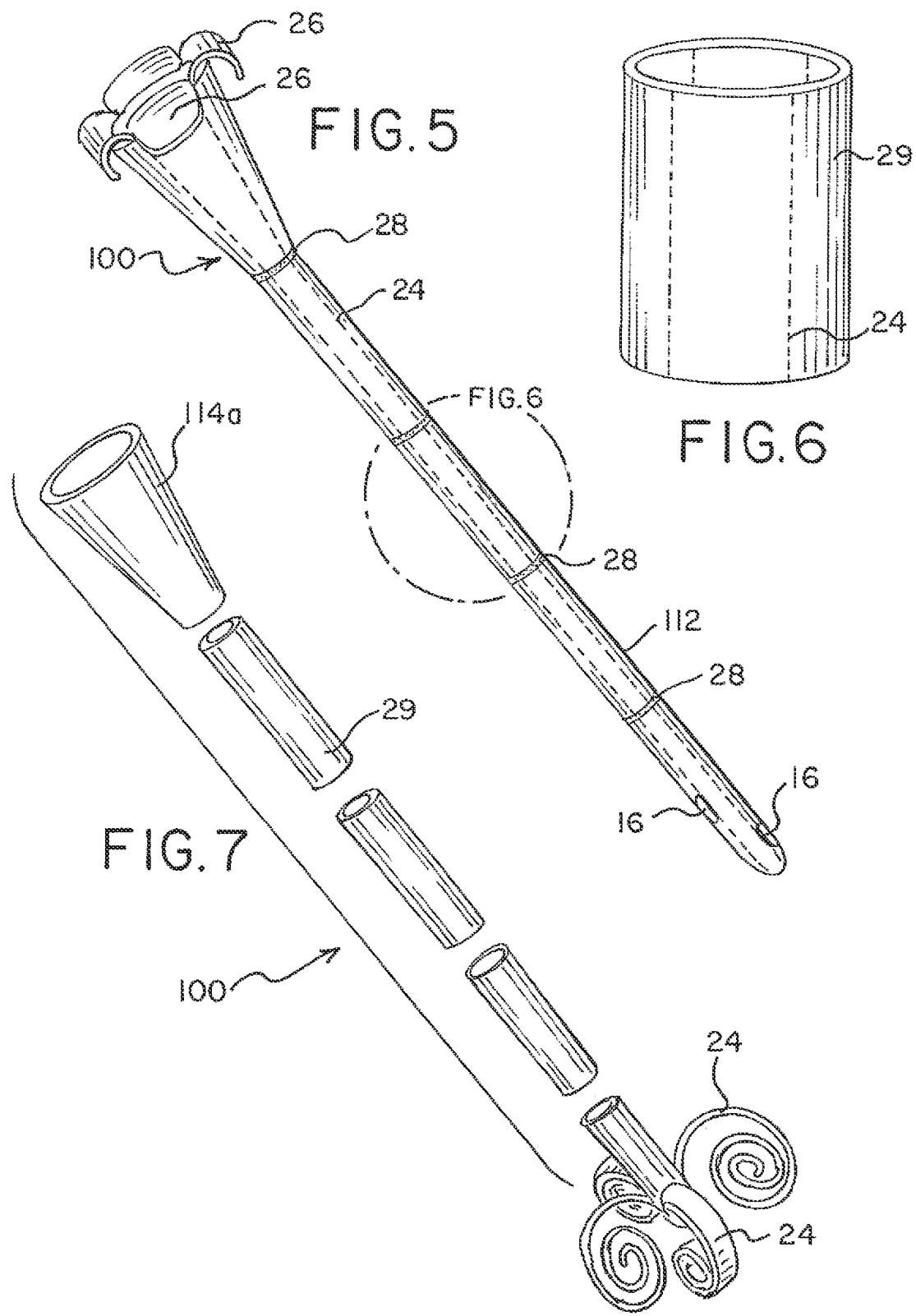

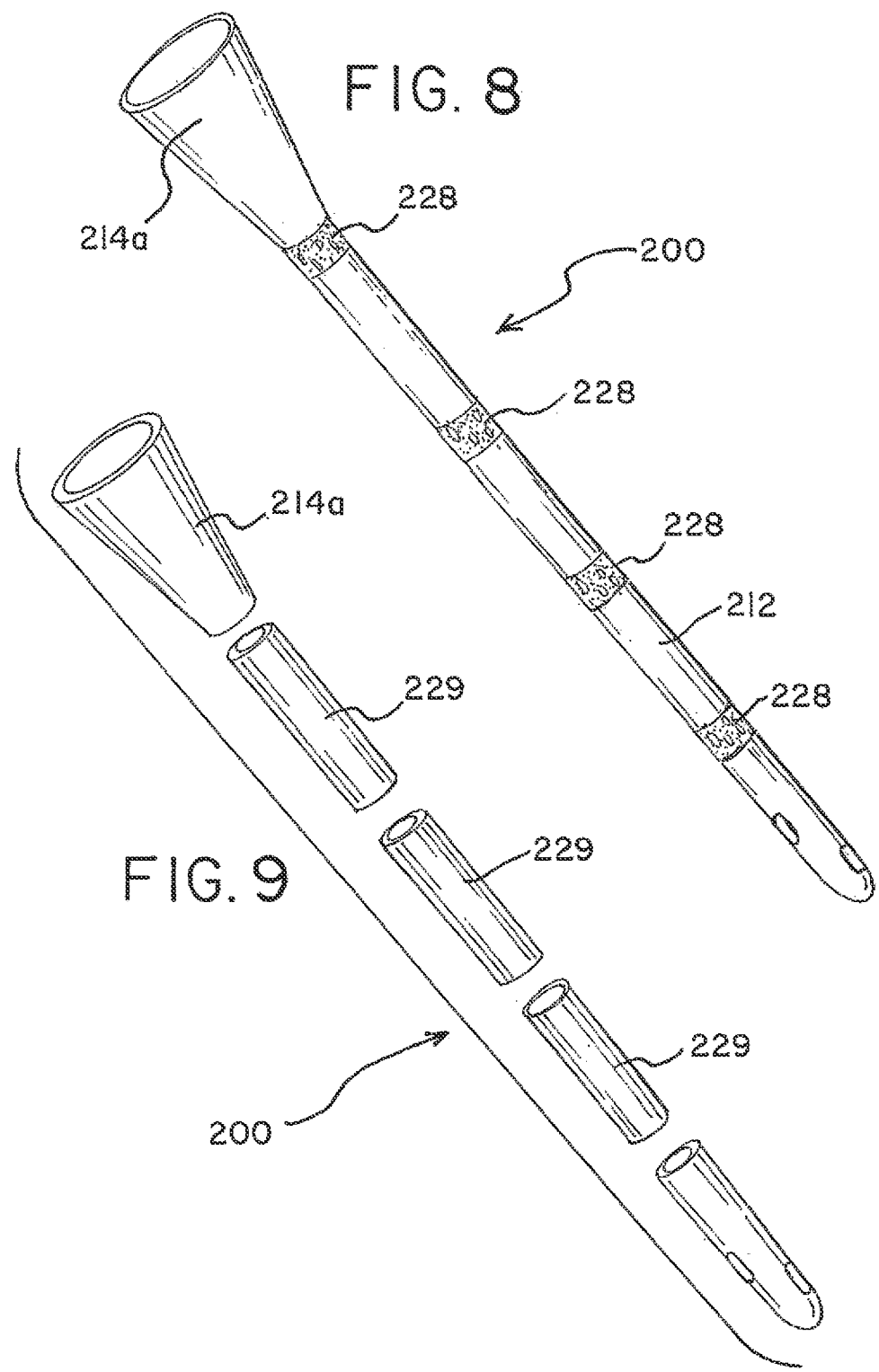

FLUSHABLE DISINTEGRATION CATHETER

CROSS-REFERENCE TO RELATED APPLICATIONS

This is a Divisional Application of U.S. National Stage application Ser. No. 15/103,399, filed Jun. 10, 2016 which is the U.S. National Application of International Application No. PCT/US14/69530, filed Dec. 10, 2014 which claims the benefit of and priority to U.S. Provisional Patent Application Ser. Nos. 61/915,311 and 61/915,396, both filed Dec. 12, 2013, and U.S. Provisional Patent Application Ser. No. 62/011,337, Filed Jun. 12, 2014, the disclosures of all of which are hereby incorporated by reference in their entireties.

FIELD OF THE DISCLOSURE

The present disclosure is directed to medical devices such as urinary catheters that after use may be disposed of by flushing down a toilet. More particularly, the present disclosure is directed to flushable catheters which are fragmentable and/or disintegrable so as to facilitate movement of the catheter through the sanitary system.

BACKGROUND

Intermittent catheters are commonly used by those who suffer from various abnormalities of the urinary system, such as urinary incontinence. Such catheters typically include an elongated shaft that is inserted into and through the urethra to access the bladder. With the advent of intermittent catheters, individuals with urinary system abnormalities can self-insert and self-remove intermittent catheters several times a day. Such catheters typically include a shaft made from non-biodegradable polymeric materials, such as non-biodegradable thermoplastics. One drawback associated with such non-biodegradable catheters is that while they are intended for disposal, they are not eco-friendly in that the non-biodegradable materials of the catheter may take several years to degrade.

Individuals who use intermittent catheters to drain their bladders several times a day often use such catheters at home and in public restrooms. Intermittent catheterization involves inserting the elongated shaft of the catheter through the urethra and into the bladder. Urine is drained from the bladder through the catheter and into a waste receptacle, such as a toilet or collection bag. After the bladder has been drained, the catheter is typically disposed of in a solid waste container. Often, particularly in a public restroom, it is difficult to find a suitable waste container to discreetly dispose of the used catheter. In addition, if the user has to carry the catheter some distance to a waste container, there may be some risk of leakage or spillage of bodily fluids. Moreover, the user may be uncomfortable or embarrassed by having to carry a used catheter to the waste container, particularly in public places. In such situations, the user may attempt to dispose of the catheter by flushing it down the toilet. Not all urinary catheters are compact or readily compactable. For example, urinary catheters used by males are substantially longer than those used by females. An intermittent urinary catheter for an adult male can be as long as 40 cm. Flushing such catheters down the toilet can cause significant plumbing problems, such as clogging. Inasmuch as the catheters are non-water disintegrable, flushing male or female urinary catheters down the toilet also raises environmental concerns.

More recently, there has been increased interest in providing flushable catheters which are made from materials that structurally disintegrate when contacted with water, e.g., materials that are dissolvable, degradable and/or undergo hydrolysis. Such catheters are intended to be flushed down the toilet after use and dissolve, degrade or otherwise break down while passing through the sanitary system. Inasmuch as flushable catheters must at least substantially maintain structural integrity during use (i.e., during insertion into the urethra, drainage of urine and removal from the urethra), the water disintegrable materials typically chosen are those with a slower degradation or dissolution rate and are such that the catheter does not substantially disintegrate until after being disposed of in the sanitary system for some time. Thus, when a flushable catheter is placed within the toilet for disposal, the structure of the catheter usually is still substantially intact and will remain substantially intact during flushing of the catheter for disposal thereof.

When a catheter is disposed of by flushing down a toilet, the force of the siphon and turbulent water current during flushing often may not carry or move the catheter down the toilet and into the pipes of the sewer system and the catheter remains, as a whole, in the toilet bowl after flushing. Additionally, because of the geometry of a typical urinary catheter, the force or energy of the flushing water may not sufficiently impinge on the catheter to propel it down the toilet. This may be especially problematic with the now more common water conserving low flush or low flow toilets. In such instances, the user may be required to flush the toilet multiple times or just leave the catheter in the toilet, which may be embarrassing especially when using a public restroom.

Thus, while flushable catheters will eventually disintegrate (e.g., dissolve, degrade or hydrolyze) after being placed within a toilet, it may be difficult to physically flush the catheter down the toilet for any number of reasons, which may result in the catheter remaining in the toilet bowl even after multiple flushes and ultimately cause embarrassment to the catheter user.

Accordingly, the present disclosure provides flushable urinary catheters that are disintegrable and also fragmentable, thereby allowing movement of the used catheter out of the toilet and through the sanitary system during flushing.

SUMMARY

In one aspect, the present disclosure is directed to a medical device that includes a body-insertable portion and a non-insertable portion wherein at least said body-insertable portion is made at least in part of a material selected to (a) retain the body-insertable portion intact when inserted within the body of a subject, and (b) fragment into multiple pieces after the device has been removed from the body and exposed to a selected condition at the time of disposal.

In another aspect, the present disclosure is directed to a flushable medical device system. The system includes a medical device assembly including a body-insertable portion and a non-insertable portion. At least the body-insertable portion is made at least in part of a material that is fragmentable into multiple fragments under a selected condition. The system also includes an agent selected to promote fragmentation of the device.

In another aspect, the present disclosure is directed to a method of disposing a used medical device including a body-insertable portion and a non-insertable portion wherein at least said body-insertable portion is made at least in part of a material that is fragmentable into multiple fragments. The method may include (a) contacting the used medical device with a solvent and (b) fragmenting the device into multiple fragments.

In a further aspect, the present disclosure is directed to a method of making a flushable medical device assembly. The method may include compounding a water soluble material with a filler selected to release thermal energy upon contact with water to provide a compounded material. The method may further include pelletizing the compounded material and molding the compounded material into a desired component of a medical device assembly.

BRIEF DESCRIPTION OF THE DRAWINGS

FIG. 1 is a perspective view of one embodiment of a medical device, such as a catheter, in accordance with the present disclosure;

FIG. 2 is a representative view of a medical device system, including the device, such as a catheter, in combination with an agent, whereby the combination of a liquid and the agent provide an environment that promotes fragmentation;

FIG. 3 is a perspective view of an embodiment of a flushable catheter system in accordance with the present disclosure;

FIG. 4 is a perspective view of another embodiment of a flushable catheter system in accordance with the present disclosure;

FIG. 5 is a perspective view of a further embodiment of a medical device, such as a catheter, in accordance with the present disclosure;

FIG. 6 is a partial view of the medical device of FIG. 5;

FIG. 7 is a perspective view of the medical device of FIG. 5 in a fragmented state;

FIG. 8 is a perspective view of another embodiment of a medical device, such as a catheter, in accordance with the present disclosure; and FIG. 9 is a perspective view of the medical device of FIG. 8 in a fragmented state.

DETAILED DESCRIPTION OF THE EMBODIMENTS

With reference to the Figures, FIGS. 1 and 2 show a medical device 10 and/or a medical device system in accordance with the present disclosure. Although medical device 10 is shown in the context of a catheter assembly, such as urinary catheter, it will be understood that the following description finds application to other non-catheter medical devices. In general, as shown in FIG. 1, medical device 10 may include body-insertable portion 12 and non-insertable portion 14. At least the body-insertable portion 12 may be made of a material that retains its structural integrity during use, i.e., the time during which the body-insertable portion 12 is inserted into and resides within the patient or subject. Non-insertable portion 14, which as the name suggests, is typically not inserted into the patient or subject, need not (but may) be made of the same material used to make body-insertable portion 12.

Medical devices 10 of the type disclosed herein are preferably, but not necessarily, devices that structurally break down when contacted by water for convenient disposal through the sewer system. Medical devices (such as catheters) disclosed herein may be made from one or more materials that are affected by a fluid (for example, water, urine or fluids utilized in toilet and plumbing systems). Such materials may be water disintegratable or disintegrable materials. As used herein "water disintegratable" or "water disintegrable" materials refer to materials that are water soluble, water degradable, or water hydrolysable, and which dissolve, degrade, or otherwise break down when in contact with water over a selected period of time. In other embodiments, the material may be enzymatically hydrolysable. The water disintegrable and enzymatically hydrolysable materials are preferably flushable materials which are suitable for disposal in a toilet or sanitary system and, even more preferably, biodegradable flushable materials which may be chemically broken down by living organisms or other biological means.

Such disintegrable or enzymatically hydrolysable materials may include, for example, certain forms of polyvinyl alcohol, including but not limited to an extrudable polyvinyl alcohol, polyacrylic acids, polylactic acid, polyesters, polyglycolide, polyglycolic acid, poly lactic-co-glycolic acid, polylactide, amines, polyacrylamides, poly(N-(2-Hydroxypropyl) methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, poly-ethers, polyethylene oxide, blends of polyethylene-polypropylene glycol, carboxymethyl cellulose, guar gum, locust bean gum, hydroxyproply cellulose shellac, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly(ε-caprolactone), poly(p-dioxanone), polyhydroxyalkanoate, or combinations, blends or copolymers of any of the above materials. The water disintegratable materials may also be any of those that are included in certified flushable products that meet the National Sanitation Foundation standards for flushability or materials and products that meet INDA/EDANA Flushability Guidelines or the UK Water Industry Research test protocols set forth in "Test Protocol to Determine the Flushability of Disposable Products, Review of the Manufactures $3^{rd}$ Ed. Guidance Document," 2013, by Drinkwater et al. While catheters made from water disintegratable or enzymatically hydrolysable materials may be disposed of in a toilet, it is not necessary to dispose of such catheters in a toilet and such catheters may also be disposed of in normal municipal waste systems or garbage collection systems.

Flushable devices of the type described herein may have a selected density. For example, it may be preferred for the medical device 10 (such as catheter assembly) and/or its individual components (including the catheter shaft, funnel, and introducer cap assembly) to have a density in the range of approximately 0.40 g/cc to approximately 1.2 g/cc, although it is also within the scope of the present disclosure for the catheter assembly or one or more of its individual components to have a density that is outside of this range.

In one embodiment, both body-insertable portion 12 and non-insertable portion 14 are preferably made of material that is water-disintegrable when exposed to water for a period of time, although non-disintegrable materials may be used as well in certain circumstances.

In an example where medical device 10 is a catheter, as shown in FIG. 1, body-insertable portion 12 is preferably the elongated shaft that is inserted into the urethra of the patient. Shaft 12 includes an elongated, hollow, typically polymeric tube that defines a flow path therethrough. As shown in FIG. 1, body-insertable portion 12 (e.g., catheter shaft) includes apertures or eyelets 16 through which urine enters the catheter. Urine flows through shaft 12 toward a funnel 14a, which is in flow communication with the flow path of shaft 12. Funnel 14a, which is typically considered a non-insertable portion 14, may be flared with an opening at its distal end for directing fluid into a waste receptacle such as a toilet or to which a plastic urine collection container may be attached.

In accordance with the present disclosure, in addition to being water-disintegrable, at least a portion of medical device 10 may be fragmentable. More particularly, at least the material used to make body-insertable portion 12 may further include a chemical compound or agent that (1) while the catheter is in use, namely within the urethral canal of the patient, it at least substantially retains its structural integrity and remains intact, (2) but upon exposure to (one or more of) a selected condition outside the body of the subject will fragment. In one embodiment, the selected conditions may be the application of physical force to the medical device that causes fragmentation of the device prior to its introduction into the waste receptacle. In another embodiment, the selected condition may be exposure to a liquid at a selected pH. In an alternative embodiment, or in addition to the conditions described above, the selected condition may be one in which an effervescent or otherwise mildly turbulent environment is provided to promote the fragmentation and/or disintegration of device 10. In accordance with another embodiment, the selected condition may be exposure of device 10 to liquid at an elevated temperature. In accordance with the present disclosure, medical device 10 will not fragment until the body-insertable portion 12 of device 10 has been removed from the patient and the selected condition is established.

In an embodiment, medical device 10 may be provided in a medical device system that further includes an agent selected to promote fragmentation and/or establish the selected condition. The selected agent may be one that affects the pH of the liquid (e.g., water) inside the waste receptacle/toilet. Alternatively, or in addition, the agent may also be one that affects the temperature of the liquid. In a further alternative or in addition to the foregoing, the agent may be one that creates an effervescent or otherwise mildly turbulent environment that will promote disintegration.

For example, in one embodiment, the agent may be a catalyst that affects the pH of a liquid (e.g., water) in the waste receptacle (e.g., toilet). In a more specific embodiment, the agent may lower the pH of the water below its original pH and/or below a pH of about 7. In the presence of water/liquid of a lowered the pH, the material selected for medical device 10 which includes a selected chemical compound or other agent will react and, for example, create gas bubbles on the surface of the device. The bubbles create a mildly turbulent or effervescent environment which promotes the breakup of the medical device 10, resulting in multiple device fragments which are easier to flush.

As shown in FIG. 2, in one embodiment, agent/catalyst 19 may be provided as a tablet 20, whereas in other embodiments, the agent/catalyst 19 may be provided in another form that provides the selected condition, i.e. pH adjustment, temperature adjustment, etc. Tablet 20 may be provided with the packaged medical product and introduced into the liquid receptacle at the time of device disposal. Alternatively, the agent/catalyst 19 may be provided as part of medical device 10 that is integral with and/or removable from device. For example, in the case of a urinary catheter as shown in FIG. 3, agent/catalyst may be dispersed or otherwise incorporated in funnel 14a that is integral with elongated shaft 12 of catheter/device 10. Upon contact with water, the non-insertable portion 14 releases the agent/catalyst 19. In another embodiment, agent/catalyst 19 may be included or otherwise incorporated into removable cap 14b commonly used in intermittent urinary catheters, as also shown specifically in FIG. 3. In yet a further embodiment, agent/catalyst 19 may be provided in a sachet or disintegrable pouch included and packaged with medical device. In a further embodiment, agent/catalyst 19 may be part of the material of package 22 that houses device 10, as shown in FIG. 4. In this case, package 22 may also likewise be made of a disintegrable material. Introduction of the entire package 22 into the water-containing waste receptacle results in the release of agent/catalyst 19 and promotes or otherwise creates the selected condition desired to promote fragmentation of medical device 10.

In an embodiment, agent/catalyst 19 and the material selected for medical device 10 (and/or package 22), when combined with water 21 (see FIG. 2), react to create the selected condition that promotes disintegration and/or fragmentation of medical device 10. For example in one embodiment, device 10 may be made of a material that includes a compound that will react with water in the presence of an agent/catalyst 19 of the type described above. It is not necessary that the entire device 10 be made of the compound. In one embodiment, device 10 (including the body-insertable portion 12 and non-insertable portion 14) may be made of generally disintegrable material of the type described above that is blended or otherwise combined with the compound selected to react directly or indirectly with agent/catalyst 19 and allow for fragmentation and/or disintegration of medical device 10. The compound may be included in both the body-insertable portion 12 and non-insertable portion 14. The compound 18 may be dispersed (uniformly or randomly) throughout the material of one of or both of body-insertable portion 12 and non-insertable portion 14, as shown in FIGS. 1-4.

In an embodiment, the compound that is dispersed throughout the material of device 10 may be one that reacts (in some manner) when exposed to the selected condition of a certain pH, while not substantially reacting when exposed to the pH environment of that part of the body into which device 10 is introduced. Thus, the body-insertable portion 12 of device 10 remains intact while inside the body of the subject or patient and does not fragment in the pH environment of the body canal during the time of treatment. In accordance with typical self-catheterization processes, the material should remain intact for up to approximately 10 minutes. The reaction may be one that causes direct disintegration and/or fragmentation of medical device 10 and or one that creates an environment that promotes fragmentation such as the effervescent environment described above.

In one example of the medical device in accordance with the present invention disclosure, the material used for the medical device, such as catheter 10, may include a blowing agent or a chemical that reacts with selected agent/catalyst 19 or the selected condition generated by the agent/catalyst 19 (FIGS. 1-4). In a specific example, the chemical compound may be sodium bicarbonate which is introduced and dispersed either randomly or uniformly throughout the walls of device 10 and, more particularly, throughout insertable body portion 12 and optionally non-insertable portion 14. A suitable agent/catalyst 19 may therefore be one that affects the pH of the liquid (water) in the liquid receptacle by lowering the pH, causing a reaction between the acidified liquid and the sodium bicarbonate dispersed in the wall(s) of medical device 10. The reaction between the agent/catalyst 19, the liquid medium (water), and the sodium bicarbonate of the device will generate a bubbling or effervescent environment that will promote disintegration and breakup of medical device 10 into smaller fragments. An example of a suitable agent/catalyst 19 that may be used to promote fragmentation of medical device 10 without damaging the environment may be a mild acidic compound such as acetic acid.

In another embodiment, medical device 10, such as a urinary catheter, may include or be made of a composite material of a water soluble polymer containing a filler/plasticizer material. The filler/plasticizer material, when in contact with water, dissolves and releases heat. Therefore, when device 10 is introduced into the toilet and contacts the water, the filler/plasticizer releases heat, accelerating the dissolution rate of the composite material, promoting disintegration and facilitating its flushability. In one embodiment, filler/plasticizer may be substantially uniformly distributed throughout device 10. In another embodiment, filler/plasticizer may be concentrated in selected portions of device 10, thereby concentrating the release and action of thermal energy at selected points along device 10. The higher concentration of filler/plasticizer and localized action of the thermal energy may provide for fragmentation of device 10 at the selected portions, as described elsewhere in the present disclosure.

For most materials, the diffusion rate increases with temperature. The dissolution of the filler/plasticizer and the thermal energy released preferably occur within a certain time scale. Thus, fillers/plasticizers with high exothermic dissolution enthalpy, but that dissolve very slowly may be less desirable. Additionally, fillers with high exothermic dissolution enthalpy but that dissolve too fast may likewise be less desirable, as they may release the thermal energy while in contact with the urine when the bladder is being emptied.

Examples of suitable fillers that may be used in medical device 10 of this embodiment include, but are not limited to, aluminum bromide, aluminum chloride, aluminum fluoride, aluminum iodide, aluminum sulfate, beryllium bromide, beryllium chloride, beryllium iodide, beryllium sulfate, cadmium sulfate, calcium bromide, calcium iodide, chromous chloride, cobaltous bromide, cobaltus iodide, cobaltus sulfate, cupric nitrate, ferric chloride, ferrous bromide, ferrous iodide, ferrous sulfate, lithium bromide, lithium iodide, lithium chloride, magnesium bromide, magnesium chloride, magnesium iodide, magnesium sulfate, magnesium sulphide, manganic sulfate, manganous acetate, manganous bromide, manganous chloride, manganous iodide, nickel bromide, nickel chloride, nickel iodide, nickel nitrate, nickel sulphate, potassium aluminum sulfate, potassium chromium sulphate, potassium hydroxide, sodium hydroxide, sodium sulfide, strontium iodide. Other organic and inorganic solids and their corresponding enthalpies of dissolution can be found in Perry's Chemical Engineer Handbook, which is incorporated herein by reference.

In another embodiment, the use of less expensive fillers (as compared to some of the polymers described above) that typically do not result in the release of thermal energy, and foaming agents such as air, may allow for a further reduction in manufacturing costs. Examples of such less expensive fillers that typically do not result in the release thermal energy include, but are not limited to, non-water soluble compounds such as calcium carbonate and some forms of cellulose, and water-soluble compounds such as sodium chloride.

Medical devices (e.g., catheters) utilizing a water-soluble polymer and filler/plasticizer may be manufactured by, for example, (1) compounding a water soluble polymer with the filler/plasticizer using a twin screw extruder, (2) pelletizing the compounded material and (3) injection molding the compounded material into a molded component of the device, such as a catheter funnel. These polymer processes involve heating the polymer above its melting temperature. Accordingly, the resulting material must have suitable physical, chemical and biological properties such that it can be used to make urinary catheters, their package and components of a flushable, ready-to-use catheter.

In one embodiment where the compounded material is molded into a catheter funnel, the funnel may be made of a foam material that includes 50% (by volume) gas, such as air, 40% filler (such as aluminum sulfate), and 10% polyvinyl alcohol (PVOH). Such 50%/40%/10% composite as described above may dissolve faster than, for example, the same funnel made of 100% PVOH, because of the presence of filler. A 20%:50%:30% composite may also be suitable for a flushable medical device as described herein.

In another embodiment, the filler material need not be incorporated into a component but may be placed in a small PVOH sachet that is then introduced into the toilet at the same time as the catheter is being flushed. In this embodiment the sachet dissolves, water contacts the filler, and heat is released, increasing the temperature of the toilet water in which the catheter is disposed prior to flushing the device.

In another embodiment, as shown in FIGS. 5-9, medical device 100 may include fracture points 28 at which the device collapses or fragments. Fracturing at fracture points may be induced under a selected condition. The selected condition may be mechanical, physical, chemical, manual or a combination of two or more such conditions. In one embodiment, medical device 100 (such as the catheter depicted in FIGS. 5-7) may include fibers 24 that may be embedded in the wall of device 100. Fragmenting or the breakup of medical device 100 (e.g., catheter 100) makes it easier to flush the used medical device 100 down the toilet and through points of constriction in a plumbing system (e.g., U-bend). In the example of FIGS. 5-7, medical device 100 may include fibers 24 embedded within the body of device 100 and more specifically in the body-insertable portion 112 (i.e., the catheter shaft). In a specific embodiment, fibers 24 may extend along the entire length of device 100 and, more specifically, body-insertable portion 112. Fibers 24 may be provided with pull tabs 26 located at or near the distal end of the elongated catheter, such as, for example, near funnel 114a. Tabs 26 allow the user to handle medical device 100 in a hygienic manner.

In the embodiment of FIGS. 5-7, fibers 24 may further be concentrated or may converge at selected points of device 100 and more specifically of body-insertable portion 112. For example, where medical device 100 is a catheter (as depicted) fibers 24 may be concentrated at fracture points 28 at selected and spaced points along the length of body-insertable portion 112. When tabs 26 are pulled, fibers 24 are necessarily pulled away from the body of the body-insertable portion 112, thereby causing a shredding and ripping of body-insertable portion 112. This, in turn may cause body-insertable portion 112, i.e., the catheter shaft, of breaking into pieces or fragments 29, as shown in FIG. 7.

Alternatively, fracture points 28 may be provided as thin-walled and/or brittle regions of medical device 100.

Making these fracture points 28 thinner and/or brittle provides for manual fragmentation of body-insertable portion 112. Thus, in one embodiment medical device 100 may be manually and bare handedly fragmented by the user at the thinner and/or brittle fracture points prior to placement in the waste receptacle such as a toilet. The medical device may additionally but optionally be provided with a tool for pressing or severing device 100 at the fracture points prior to disposal in the waste receptacle or toilet bowl.

In another embodiment shown in FIGS. 8-9, fracture points 228 may be regions that include a higher concentration of a readily water soluble polymer material. The remainder of device 200 may be made of a material having solubility characteristics different from fracture points 228 and, thereby, dissolve at a much slower rate. This may allow device 200 to maintain its required mechanical properties and structural integrity during use, while allowing device 200 to break up or effectively melt at predefined points as soon as it comes into contact with the water. In addition, fracture points 228 may be selected on the basis that they will be less likely to have water exposure when in use by the patient but more likely to get wetted and break up or dissolve immediately or almost immediately when placed in the toilet bowl.

In another embodiment, fracture points 228 may be provided as regions pre-loaded with a chemical that reacts when it contacts water in the toilet. For example, fracture points 228 may be pre-loaded with a chemical compound such as sodium bicarbonate or a blowing agent. In accordance with previously described embodiments, acetic acid, or table vinegar, or another acidic agent may be added to the toilet water to accelerate the break-up of the catheter at these points into fragments 229 when the sodium bicarbonate or other compounds react with the acidified water. The device 100 or 200 maintains its required mechanical properties and structural integrity during the treatment period when it resides within the patient, while allowing it to break-up or fragment at predefined points when placed in contact with water (in the toilet bowl.)

The embodiments disclosed herein facilitate discrete disposal of a used medical device (and optionally its associated packaging) in a toilet without leaving waste in the trash bin. This may be particularly desirable when users catheterize in public toilet facilities or in the toilet facilities of family and friends. Catheters of the type described herein also reduce the level of physical difficulty for disposal of materials used at the end of the procedure.

Other Aspects

In a first aspect, a medical device including a body-insertable portion and a non-insertable portion is provided. At least the body-insertable portion is made at least in part of a material selected to (a) retain the body-insertable portion intact when inserted in the body of the subject, and (b) fragment into multiple pieces when outside the body and under a selected condition.

A second aspect of the present subject matter includes the medical device in accordance with the first aspect wherein the selected condition comprises contact with water.

A third aspect of the present subject matter includes the medical device in accordance with any one of the first or second aspects wherein the selected condition comprises the presence of an agent selected to promote disintegration of at least the body-insertable portion.

A fourth aspect of the present subject matter includes the medical device in accordance with the third aspect wherein the agent is separate from the device.

A fifth aspect of the present subject matter includes the medical device in accordance with the third aspect wherein the non-insertable portion contains the agent.

A sixth aspect of the present subject matter includes the medical device in accordance with any one of the first through fifth aspects wherein the selected material includes a chemical compound dispersed throughout at least the body-insertable portion.

A seventh aspect of the present subject matter includes the medical device in accordance with any one of the first through sixth aspects wherein the compound is sodium bicarbonate.

An eighth aspect of the present subject matter includes the medical device in accordance with any one of the first through sixth aspects wherein the selected condition comprises a liquid solvent having a pH of less than approximately 7.0.

A ninth aspect of the present subject matter includes the medical device in accordance with any one of the first through seventh aspects wherein the selected condition comprises an effervescent liquid environment.

A tenth aspect of the present subject matter includes the medical device in accordance with any one of the first through eighth aspects wherein the selected condition comprises a liquid of increasing temperature.

An eleventh aspect of the present subject matter includes the medical device in accordance with the first aspect wherein at least the body-insertable portion comprises a plurality of fibers embedded therein.

A twelfth aspect of the present subject matter includes the medical device in accordance with the eleventh aspect wherein the medical device includes pull tabs associated with the fibers.

A thirteenth aspect of the present subject matter includes the medical device in accordance with any one of the first through twelfth aspects wherein the body-insertable portion comprises fracture points.

A fourteenth aspect of the present subject matter includes the medical device in accordance with the thirteenth aspect wherein the fracture points include a material different from the selected material.

A fifteenth aspect of the present subject matter includes the medical device in accordance with any one of the thirteenth or fourteenth aspects wherein the fracture points have a solubility that is different from the solubility of the remainder of the body-insertable portion.

A sixteenth aspect of the present subject matter includes the medical device in accordance with any one of the thirteenth through fifteenth aspects wherein the fracture points have a thickness different from the thickness of the remainder of the body-insertable portion.

A seventeenth aspect of the present subject matter includes the medical device in accordance with any one of the first through sixteenth aspects wherein the non-insertable portion comprises a material selected to fragment into multiple pieces when under the selected condition.

In an eighteenth aspect a method of disposing of a used medical device is provided. The medical device includes a body-insertable portion and a non-insertable portion wherein at least the body-insertable portion is made at least in part of a material that is fragmentable. The method includes (a) contacting the device with a solvent and (b) fragmenting the device into multiple fragments.

A nineteenth aspect of the present subject matter includes the method in accordance with the eighteenth aspect comprising fragmenting the device prior to contacting.

A twentieth aspect of the present subject matter includes the method in accordance with any one of the eighteenth or nineteenth aspects comprising fragmenting the device at selected fracture points along the body-insertable portion.

A twenty-first aspect of the present subject matter includes the method in accordance with any one of the eighteenth through twentieth aspects comprising combining the device with a catalyst.

A twenty-second aspect of the present subject matter includes the method in accordance with the twenty-first aspect comprising adding the catalyst to the solvent before or after contacting.

A twenty-third aspect of the present subject matter includes the method in accordance with any one of the eighteenth through twenty-second aspects further comprising creating an effervescent environment.

A twenty-fourth aspect of the present subject matter includes the method in accordance with any one of the eighteenth through twenty-third aspects comprising raising the temperature of the solvent.

A twenty-fifth aspect of the present subject matter includes the method in accordance with any one of the eighteenth through twentieth aspects wherein the device comprises points of weakness distributed throughout at least the body-insertable portion.

A twenty-sixth aspect of the present subject matter includes the method in accordance with any one of the eighteenth through twenty-fifth aspects comprising removing embedded fibers from the device.

In a twenty-seventh aspect, a flushable medical device system is provided. The medical device system includes a medical device assembly including a body-insertable portion and a non-insertable portion wherein at least the body-insertable portion is made at least in part of a material that is fragmentable into multiple fragments, and an agent selected to promote fragmentation of the device.

A twenty-eighth aspect of the present subject matter includes the flushable medical device system in accordance with the twenty-seventh aspect wherein the agent is a compound that reacts with the material.

A twenty-ninth aspect of the present subject matter includes the system in accordance with the twenty-seventh aspect wherein the agent is a compound that reacts with a liquid.

A thirtieth aspect of the present subject matter includes the system in accordance with the twenty-ninth aspect wherein the liquid is water.

A thirty-first aspect of the present subject matter includes the system in accordance with any one of the twenty-seventh through thirtieth aspects wherein the agent comprises an acid.

A thirty-second aspect of the present subject matter includes the system in accordance with any one of the twenty-seventh through thirtieth aspects wherein the agent is selected to raise the temperature of the liquid.

A thirty-third aspect of the present subject matter includes a system in accordance with any one of the twenty-seventh through thirtieth aspects wherein the agent is provided in the form of a tablet.

A thirty-fourth aspect of the present subject matter includes the system in accordance with any one of the twenty-seventh through thirtieth aspects wherein the agent is provided in a part of the device assembly.

A thirty-fifth aspect of the present subject matter includes the system in accordance with any one of the twenty-seventh through thirty-fourth aspects further comprising a package wherein the agent is provided in the package.

A thirty-sixth aspect of the present subject matter includes the system in accordance with any one of the twenty-seventh through thirty-fifth aspects wherein at least the body-insertable portion comprises sodium bicarbonate.

In a thirty-seventh aspect, a method of making a flushable medical device assembly is provided. The method includes (a) compounding a water soluble material with a filler selected to release thermal energy upon contact with water to provide a compounded material, (b) pelletizing the compounded material, and (c) molding the compounded material into a desired component of a medical device assembly.

A thirty-eighth aspect of the present subject matter includes the method in accordance with the thirty-seventh aspect further comprising incorporating the molded component into the medical device.

A thirty-ninth aspect of the present subject matter includes the method in accordance with any one of the thirty-seventh or thirty-eighth aspects wherein the water soluble material is heated to a temperature above its melting point.

A fortieth aspect of the present subject matter includes the method in accordance with any one of the thirty-eighth or thirty-ninth aspects wherein the desired component comprises a foam material.

A forty-first aspect of the present subject matter includes the method in accordance with the fortieth aspect wherein the material comprises about 50% gas by volume.

A forty-second aspect of the present subject matter includes the method in accordance with the forty-first aspect wherein the desired component further comprises a polymeric material.

A forty-third aspect of the present subject matter includes the method in accordance with the forty-second aspect wherein the polymeric material comprises polyvinyl alcohol.

A forty-fourth aspect of the present subject matter includes the method in accordance with any one of the fortieth through forty-third aspects wherein the desired component comprises a foam comprising gas, filler, and a polymer in a ratio of 20:30:50.

A forty-fifth aspect of the present subject matter includes the method in accordance with any one of the thirty-seventh through forty-fourth aspects wherein the medical device is a urinary catheter, the method comprising molding the compounded material into a catheter funnel.

What is claimed is:

1. A flushable medical device system, comprising:
   a) a medical device assembly including a body-insertable portion and a non-insertable portion wherein at least said body-insertable portion is made at least in part of a water disintegratable material that is fragmentable into multiple fragments, wherein a chemical compound is dispersed throughout the water disintegratable material; and
   b) a catalyst that reacts with the chemical compound to promote fragmentation of said body-insertable portion at the time of disposal,
   wherein the catalyst is separate from the body-insertable portion.

2. The system of claim 1 wherein said catalyst is a compound that reacts with said material.

3. The system of claim 1 wherein said catalyst is a compound that reacts with a liquid.

4. The system of claim 1 wherein said catalyst comprises an acid.

5. The system of claim 1 wherein said catalyst is selected to raise the temperature of said liquid.

6. The system of claim 1 wherein said catalyst is provided in the form of a tablet.

7. The system of claim 1 wherein said catalyst is provided in the non-insertable portion of said device assembly.

8. The system of claim 1 further comprising a package having the medical device assembly contained therein, wherein said catalyst is provided in said package containing the medical device assembly.

9. The system of claim 1 wherein said chemical compound comprises sodium bicarbonate.

10. The system of claim 8, wherein the package containing the medical assembly includes a cavity and the medical device assembly and the catalyst is contained within the cavity.

11. The system of claim 8, wherein the package comprises a packaging material and the catalyst is part of the packaging material.

12. The system of claim 8, wherein the package comprises a disintegrable packaging material.

13. The system of claim 1, wherein the chemical compound defines fracture points.

14. The system of claim 1, wherein the catalyst is in a dissolvable sachet.

15. A flushable urinary catheter product, comprising:
  a) a catheter assembly including a body-insertable portion and a non-insertable portion wherein at least said body-insertable portion is made at least in part of a water disintegratable material that is fragmentable into multiple fragments, wherein a chemical compound is dispersed throughout the water disintegratable material; and
  b) a catalyst that reacts with the chemical compound to promote fragmentation of said body-insertable portion at the time of disposal, wherein the catalyst is separate from the body-insertable portion.

16. The product of claim 15 wherein said catalyst is a compound that reacts with said material.

17. The product of claim 15 wherein said catalyst is a compound that reacts with a liquid.

18. The product of claim 15 wherein said catalyst comprises an acid.

19. The product of claim 15 wherein said catalyst is provided in the form of a tablet.

20. The product of claim 15 wherein said catalyst is provided in the non-insertable portion of said device assembly.

21. The product of claim 15 further comprising a package having the medical device assembly contained therein, wherein said catalyst is provided in said package containing the medical device assembly.

22. The product of claim 15 wherein said chemical compound comprises sodium bicarbonate.

23. The product of claim 15, wherein the chemical compound defines fracture points.

24. The product of claim 15, wherein the catalyst is in a dissolvable sachet.

* * * * *